(12) United States Patent
King

(10) Patent No.: US 10,170,154 B2
(45) Date of Patent: Jan. 1, 2019

(54) SYMMETRICALLY MIRRORED VIDEO SEGMENT

(71) Applicant: Virtual Dreamware, LLC, Jupiter, FL (US)

(72) Inventor: William King, Jupiter, FL (US)

(73) Assignee: Virtual Dreamware, LLC, Jupiter, FL (US)

( * ) Notice: Subject to any disclaimer, the term of this patent is extended or adjusted under 35 U.S.C. 154(b) by 202 days.

(21) Appl. No.: 15/334,359

(22) Filed: Oct. 26, 2016

(65) Prior Publication Data

US 2017/0140790 A1 May 18, 2017

Related U.S. Application Data

(60) Provisional application No. 62/255,712, filed on Nov. 16, 2015.

(51) Int. Cl.
| | | |
|---|---|---|
| *H04N 7/00* | (2011.01) | |
| *H04N 7/01* | (2006.01) | |
| *H04N 5/265* | (2006.01) | |
| *G11B 27/031* | (2006.01) | |
| *G11B 27/034* | (2006.01) | |

(52) U.S. Cl.
CPC .......... *G11B 27/034* (2013.01); *G11B 27/031* (2013.01); *H04N 7/002* (2013.01); *A61C 2203/00* (2013.01); *H04N 5/265* (2013.01); *H04N 7/0122* (2013.01)

(58) Field of Classification Search
CPC .............. A61C 2203/00; G11B 27/034; G11B 27/031; H04N 7/002; H04N 5/265; H04N 7/0122
See application file for complete search history.

(56) References Cited

U.S. PATENT DOCUMENTS

| | | |
|---|---|---|
| 5,510,832 A | 4/1996 | Garcia |
| 6,108,005 A | 8/2000 | Starks et al. |
| 7,321,374 B2 | 1/2008 | Naske |
| 8,780,998 B2 | 7/2014 | Pandit et al. |
| 2011/0280316 A1 | 11/2011 | Chen et al. |

*Primary Examiner* — Huy T Nguyen
(74) *Attorney, Agent, or Firm* — McHale & Slavin, P.A.

(57) ABSTRACT

A method for dividing one 720×1080, 1080×1920, 2K, 4K, 8K or a 12K video segment into two equal segments using a mathematical aspect ratio calculation which by combining two equal 720×1080, 1080×1920, 2K, 4K, 8K or 12K video segments to create one symmetrically mirrored 720×1080, 1080×1920, 2K, 4K, 8K or a 12K video segment to make one three second to thirty minute video to be up loaded and played within video glasses, 3D software and 3D video glasses, 3D parallax software, micro SD memory cards, HD televsions, 3D televisions, virtual reality software and hardware, mobile media applications, computers and all video streaming internet applications including widescreen cinema standard and IMAX theatrical projections.

11 Claims, 2 Drawing Sheets

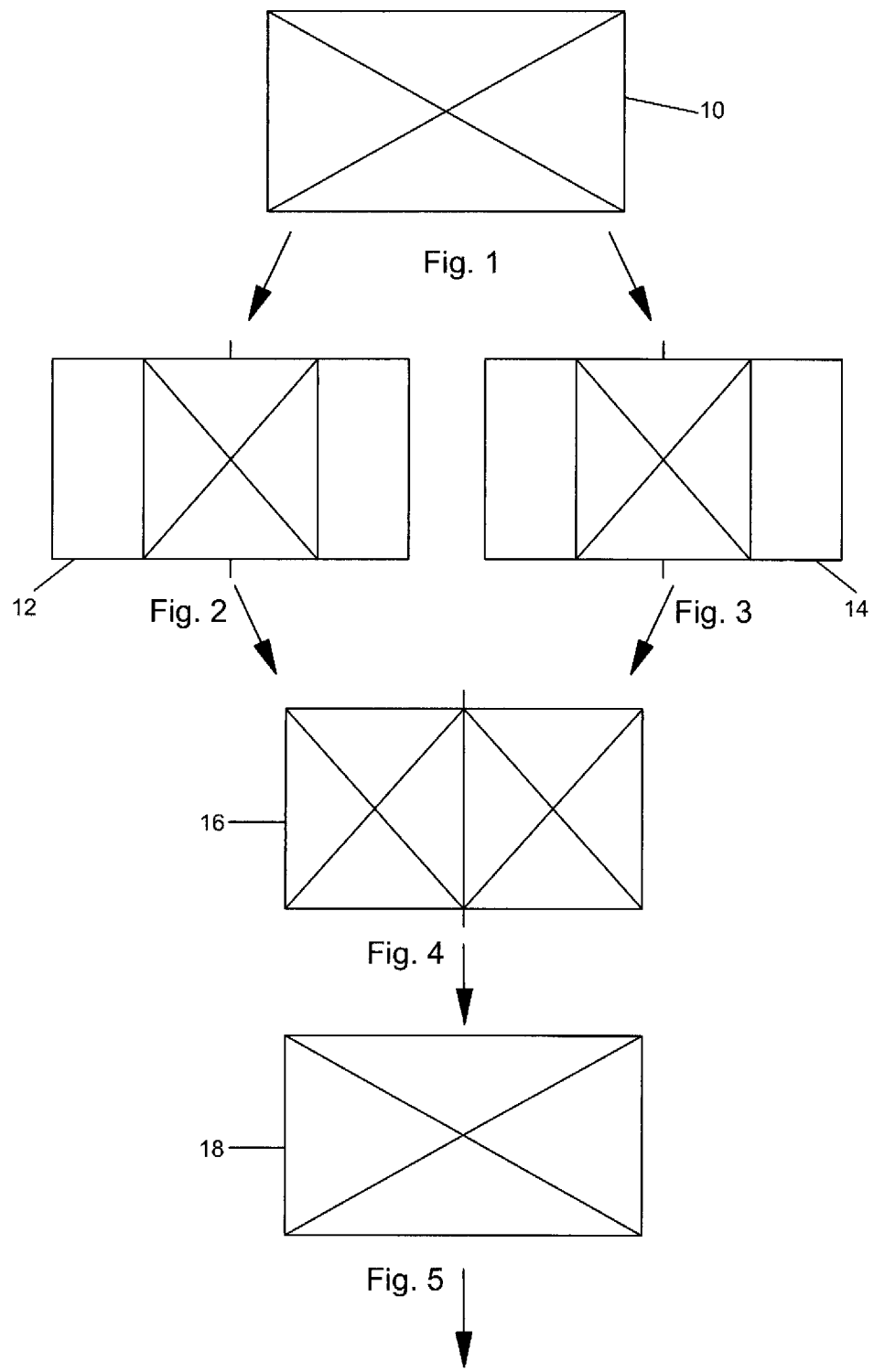

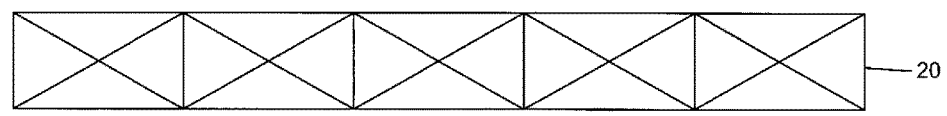
Fig. 6
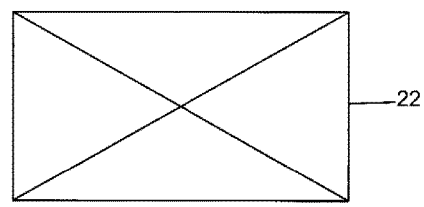
Fig. 7
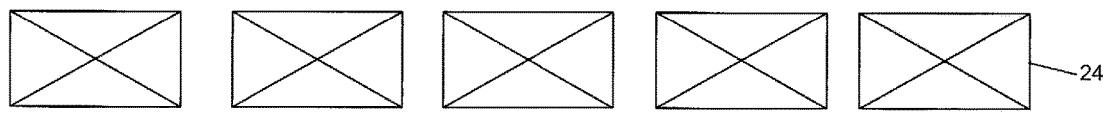
Fig. 8

SYMMETRICALLY MIRRORED VIDEO SEGMENT

PRIORITY CLAIM

In accordance with 37 C.F.R. § 1.76, a claim of priority is included in an Application Data Sheet filed concurrently herewith. Accordingly, the present invention claims priority of U.S. Provisional Patent Application No. 62/255,712, entitled SYMMETRICALLY MIRRORED VIDEO SEGMENT filed Nov. 16, 2015, the contents of which is incorporated herein by reference.

FIELD OF THE INVENTION

This invention is related to the field of high definition video and in particular to a method of creating a symmetrically mirrored high definition video.

BACKGROUND OF THE INVENTION

Video programs have the ability to induce various reactions in the mind of a viewer. The reactions could be emotions such as feeling happy or sad. It has further been recognized that certain programming techniques can induce various brain wave frequencies in the viewer. Such techniques include clarity of the picture and sterovison to relieve eye stress and bring the viewer into a relaxed state of being.

U.S. Pat. No. 5,510,832 discloses a method of synthesizing a three-dimensional image from a two dimensional image.

U.S. Pat. No. 6,108,005 discloses a method for generating stereo images in which at least two images are generated based on a loaded image. At least one of the generated images is adjusted (enlarged, reduced, rotated, displace, or changed) relative to the laded image in such a way that at least parts of the image are displaced relative to other parts of the image in comparison to corresponding parts in another image.

U.S. Pat. No. 7,321,374 discloses a method for generating three-dimensional images based on a sequence of two-dimensional images characterized by the steps of: analyzing a two-dimensional image with respect to its scene type, selecting a deformation assigned to the defined scene type with which the two-dimensional image is deformed, deforming the two-dimensional image and transmitting the deformed two-dimensional image to at least one viewing.

U.S. Pat. No. 8,780,998 discloses a video decoding and encoding process that takes multiple pictures that are flipped in one or more horizontal or vertical directions.

U.S. Publication No. 2011/0280316 discloses an asymmetric frame of a coded video bit stream which includes a full resolution picture of a left view and a reduced resolution picture of a right view, where the left and right views form a stereo view pair for three-dimensional video playback.

What is needed in the art is a method of making a video program configured to stimulate a user's brain to induce various brain wave frequencies such as bringing the viewer into a relaxed state of being.

SUMMARY OF THE INVENTION

A method for dividing one 720×1080, 1080×1920, 2K, 4K, 8K or a 12K video segment with a (1.43:1, 1.78:1, 1.85:1, 2.35:1 or a 2.76:1) aspect ratio into two equal segments using a mathematical aspect ratio calculation, and combining two equal video segments to create one symmetrically mirrored 720×1080, 1080×1920, 2K, 4K, 8K or a 12K video segment with an (1.43:1, 1.78:1, 1.85:1, 2.35:1 or a 2.76:1) aspect ratio video segment that can be combined withother perfectly symmetrically mirrored video segments to make one three second to thirty minute video.

An objective of the instant invention is to provide a method of making a three second to thirty minute video with the purpose of bringing the viewer into a relaxed state of being.

Another objective of the invention is to teach a method of making symmetrically mirrored 720×1080, 1080×1920, 2K, 4K, 8K or 12K video segments with an (1.43:1, 1.78:1, 1.85:1, 2.35:1 or a 2.76:1) aspect ratio that are used with video glasses, 3D software and 3D video glasses, 3D parallax software, micro SD memory cards, HD televsions, 3D televisions, virtual reality software and hardware, mobile media applications, computers, all video streaming internet applications and services, widescreen cinema, standard and IMAX movies.

Yet another objective of the invention is to teach a method of making one to 60 symmetrically mirrored 720×1080, 1080×1920, 2K, 4K, 8K or 12K video segments with a (1.43:1, 1.78:1, 1.85:1, 2.35:1 or a 2.76:1) aspect ratio that can be placed together with sound and an audio soundtrack in a computer based video editing software to create one three second to thirty minute video program.

Yet another objective of the instant system is to teach the method of dividing one (1.43:1, 1.78:1, 1.85:1, 2.35:1 or a 2.76:1) aspect ratio, 720×1080, 1080×1920, 2K, 4K, or 8K or a 12K video segment into two equal segments, compressing the two equal segments using an aspect ratio equation that when converted, creates a single symmetrical (1.43:1, 1.78:1, 1.85:1, 2.35:1 or a 2.76:1) aspect ratio, 720×1080, 1080×1920, 2K, 4K, 8K or a 12K mirrored video segment.

Other objectives and further advantages and benefits associated with this invention will be apparent to those skilled in the art from the description, examples and claims which follow.

BRIEF DESCRIPTION OF THE DRAWINGS

FIG. 1 is a pictorial illustration of a video segment;

FIG. 2 is a pictorial illustration of a video segment that has been reduced 50% horizontally within the given aspect ration;

FIG. 3 is a pictorial illustration of the same video segment as FIG. 2, which is horizontally flipped to the left side of the given aspect ratio;

FIG. 4 is a pictorial illustration of both horizontally reduced video segments positioned at the extreme left and right edge of the given aspect ration, which places the two video segments side by side at the middle of the video screen;

FIG. 5 is a pictorial illustration of a combined symmetrically mirrored video segment;

FIG. 6 is a pictorial illustration of multiple symmetrically mirrored video segments;

FIG. 7 is a pictorial illustration of a three second to thirty minute video; and FIG. 8 is a pictorial illustration of various hardware component uploads.

DETAILED DESCRIPTION OF THE PREFERRED EMBODIMENT

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

The instant system and method for dividing one (1.43:1, 1.78:1, 1.85:1, 2.35:1 or a 2.76:1) aspect ratio, 720×1080, 1080×1920, 2K, 4K, 8K or a 12K video segment (10) into two equal segments, compressing these two equal segments (12, 14) using an aspect ratio equation that when converted creates a symmetrical (1.43:1, 1.78:1, 1.85:1, 2.35:1 or a 2.76:1) aspect ratio, 720×1080, 1080×1920, 2K, 4K, 8K or a 12K mirrored video segment (16). These segments are then combined with other symmetrically mirrored video segments (18), natural sounds and an audio soundtrack in a computer based video editing software to create a three second to thirty minute (1.43:1, 1.78:1, 1.85:1, 2.35:1 or a 2.76:1) aspect ratio, 720×1080, 1080×1920, 2K, 4K, 8K or a 12K video (20). This video is then compressed (22) into specific formats to be played within video glasses, 3D software and 3D video glasses, 3D parallax software, micro SD memory cards, HD televisions, 3D televisions, virtual reality software and hardware, mobile media applications, computers and all video streaming internet applications and services, widescreen cinema, standard and IMAX movies (24).

The three second to thirty minute video program is created with the purpose of bringing the viewer into a relaxed state of being. The mathematical aspect ratio formula to produce this symmetrically mirrored video segment is as follows. Referring to FIG. 1, an original 720×1080, 1080×1920, 2K, 4K, 8K or a 12K, (1.43:1, 1.78:1, 1.85:1, 2.35:1 or a 2.76:1) aspect ratio video segment is captured. Referring to FIG. 2, the original (1.43:1, 1.78:1, 1.85:1, 2.35:1 or a 2.76:1) aspect ratio is maintained and a %50 reduction is applied to the horizontal field of view to the direct center of the 720×1080, 1080×1920, 2K, 4K, 8K or a 12K field of view. Referring to FIG. 3, the original (1.43:1, 1.78:1, 1.85:1, 2.35:1 or a 2.76:1) aspect ratio is maintained and a %50 reduction is applied to the horizontal field of view to the direct center of the 720×1080, 1080×1920, 2K, 4K, 8K or a 12K field of view. The video segment is then flipped horizontally to the left.

For example, odontophobia is a unique phobia with special psychosomatic components that impact on the dental health of the odontophobic persons. Researchers have found that a number of factors contribute to the etiology of dental fears. Four causes of fear include conditioning, an innate predisposition, physiological differences, and fear due to direct stimulation or nonassociative perspective. It is not only just pain that makes many patients uncomfortable. The plethora of instrument sounds and smells, the violation of personal space, and experiencing unusual sensations, can make many feel anxious and or fearful.

Certain aspects of the physical environment also play an important role in alleviating dental fear. For example, playing television and music in the background can help patients by removing and replacing stimuli which can trigger feelings of fear from classical conditioning. Some anxious patients respond well to more obvious distraction techniques such as watching movies, listening to music, or even using virtual-reality headsets during treatment. There are numerous specialized behavioral treatments currently available to assist in the reduction of dental anxiety. These include, but are not limited to, teaching individuals relaxation techniques, such as diaphragmatic breathing and progressive muscle relaxation, as well as cognitive, or thought-based techniques, such as cognitive restructuring and guided imagery. These processes are time consuming and many individuals are not able to perform the modality. There is no mistaking the prevalence of anxiety and stress in dental patients, and therefore there is every reason to pursue every treatment modality that may positively impact patients and decrease the presence or degree of stress and anxiety while undergoing dental treatments. The instant invention has a unique adaptation for use with dental patients.

Referring to FIG. 4, two horizontally reduced 720×1080, 1080×1920, 2K, 4K, 8K or 12K video segments within one 720×1080, 1080×1920, 2K, 4K, 8K or 12K, (1.43:1, 1.78:1, 1.85:1, 2.35:1 or a 2.76:1) aspect ratio field of view. The duplicated horizontally (flipped) video segment is moved to the edge of the right side of the 720×1080, 1080×1920, 2K, 4K, 8K or a 12K, (1.43:1, 1.78:1, 1.85:1, 2.35:1 or a 2.76:1) aspect ratio field of view. The original image is then moved to the edge of the left side of the 720×1080, 1080×1920, 2K, 4K, 8K or 12K, (1.43:1, 1.78:1, 1.85:1, 2.35:1 or a 2.76:1) aspect ratio field of view. Referring to FIG. 5, these two altered video segments are place side by side at the center of a 720×1080, 1080×1920, 2K, 4K, or 8K or a 12K, (1.43:1, 1.78:1, 1.85:1, 2.35:1 or a 2.76:1) field of view. The result of this mathematical aspect ratio formula creates one symmetrically mirrored 720×1080, 1080×1920, 2K, 4K, 8K or a 12K, (1.43:1, 1.78:1, 1.85:1, 2.35:1 or a 2.76:1) aspect ratio video segment.

Referring to FIG. 6, the method permits up to one to sixty symmetrically mirrored 720×1080, 1080×1920, 2K, 4K, 8K or 12K, (1.43:1, 1.78:1, 1.85:1, 2.35:1 or 2.76:1) video segments together with sound and an audio soundtrack in a computer based video editing software to create one three second to thirty minute video program.

Referring to FIGS. 7 and 8, the completed three second to thirty minute video program is compressed into a selected and specific format to be uploaded into multiple hardware devices. The video programs are created with the purpose of bringing the viewer into a relaxed state of being. The symmetrically mirrored 720×1080, 1080×1920, 2K, 4K, 8K or a 12K, (1.43:1, 1.78:1, 1.85:1, 2.35:1 or 2.76:1) video segments are uploaded to video glasses, 3D software and 3D video glasses, 3D parallax software, micro SD memory cards, HD televsions, 3D televisions, virtual reality software and hardware, mobile media applications, computers, all video streaming internet applications and services, widescreen cinema standard and IMAX theatrical projections.

The instruments used in a basic application for odontophobia include a high definition audiovisual device that resembles a pair of glasses with audio ear buds attached. The device projects a cinematic stress/anxiety reduction experience, which is a mix of artistically filmed nature inspired video segments, coupled with melodic natural soundtracks that engage the senses. Each program is specifically designed to reduce stress and anxiety levels while accessing the subconscious mind through increased control of the brain's alpha waves.

Effectiveness can be measured by the Corah's Dental Anxiety Scale which evaluates levels of dental anxiety and stress with 7 questions that are scored by the participant with a Likert-type scale (0-5). Each item is categorized as an indicator or anxiety or stress, and includes a scoring sheet the scorer uses to identify the resulting data. Under such conditions it was found that the instant invention improves internal dialogue associated with anxiety and stress, and helps individuals relieve anxiety and stress associated with dental procedures.

The method for producing a symmetrically mirrored video segment consists of selecting a video segment; dividing said video segment into two equal segments; reducing said two equal segments with an aspect ratio equation that when converted creates a symmetrical mirrored video segment; adding an audio soundtrack to said symmetrical mirrored video segment; and playing said symmetrical mirrored video segment on a viewing device.

The video segment is selected from the 720×1080, 1080×1920, 2K, 4K, or 8K or 12K video segments having an aspect ratio of: (1.43:1, 1.78:1, 1.85:1, 2.35:1 or 2.76:1). Natural sounds can be added using a computer based video editing software to create said video.

The mirrored video segment has an aspect ratio equation that when converted creates a symmetrical 720×1080, 1080×1920, 2K, 4K, 8K or 12K, (1.43:1, 1.78:1, 1.85:1, 2.35:1 or a 2.76:1), field of view. The aspect ratio 1.43:1, 1.78:1, 1.85:1, 2.35:1 or 2.76:1 is maintained and a %50 reduction is applied to the horizontal field of view to the direct center of the 720×1080, 1080×1920, 2K, 4K, 8K or a 12K field of view.

Alternatively, the aspect ratio 1.43:1, 1.78:1, 1.85:1, 2.35:1 or 2.76:1 is maintained and the video segment is flipped horizontally and a %50 reduction is applied to the horizontal field of view to the direct center of the 720×1080, 1080×1920, 2K, 4K, 8K or a 12K field of view.

The flipped video segment can be moved to the right corner of the 720×1080, 1080×1920, 2K, 4K, 8K or 12K, (1.43:1, 1.78:1, 1.85:1, 2.35:1 or a 2.76:1) aspect ratio field of view and the original segment is moved to the left corner of the 720×1080, 1080×1920, 2K, 4K, 8K or 12K, (1.43:1, 1.78:1, 1.85:1, 2.35:1 or a 2.76:1) aspect ratio field of view.

The flipped and original segments are place side by side at the center of a 720×1080, 1080×1920, 2K, 4K, 8K or a 12K field of view to create one symmetrically mirrored video segment, and the symmetrically mirrored video segment can be combined with other symmetrically mirrored video segments.

The average symmetrically mirrored video segment is between three seconds and thirty minutes long and can be played on a device selected from the group of: video glasses, 3D software and 3D video glasses, 3D parallax software, micro SD memory cards, HD televsions, 3D televisions, virtual reality software and hardware, mobile media, computers and video streaming internet, widescreen cinema standard and IMAX theatrical projections.

A case study was conducted at a Dental Center to determine the level of efficacy to reduce anxiety and stress for individuals who were waiting to receive dental treatment. Up to thirty minutes of audio visual programming was administered prior using the instant invention to one dental treatment. The subject's effectiveness was monitored using a pre and post dental anxiety and stress assessment survey. The instruments used in the study included an audiovisual device that resembles a pair of glasses with audio ear buds attached. The video glasses cover both eyes of the patient, limiting outside viewing to a minimum. The audio portion was played simultaneously through both the right and left earbuds. The volume was set to a level of 21 out of a maximum 30. The sequential order of the uploaded 15-minute program was predetermined allowing each patient to experience the same 15-minute program prior to their dental treatment. The only independent variable to the case study was the length of time a patient viewed the program. There was a minimum of two and a maximum of four of the same 15-minute program experienced by each patient.

The device projects a cinematic stress/anxiety reduction experience in accordance with the teachings of the instant invention, namely a mix of artistically filmed nature inspired video segments, coupled with melodic natural soundtracks. Each program is specifically designed to reduce stress and anxiety levels while accessing the subconscious mind through increased control of the brain's alpha waves. The Corah's Dental Anxiety Scale (DAS-R) survey evaluates levels of dental anxiety and stress with 7 questions that are scored by the participant with a Likert-type scale (0-5). Each item is categorized as an indicator or anxiety or stress, and includes a scoring sheet the scorer uses to identify the resulting data. The Corah's Dental Anxiety Scale (DAS-R) survey was utilized to measure the dependent variable and assess levels of anxiety before and after each participants one use of Numbered scores for dental anxiety were tabulated to give each participant a Pre and Post Anxiety Scale Number. These anxiety scale numbers are as follows: 0-15 Moderate Anxiety, 16-23 High Anxiety, 24-35 Severe Anxiety. Data was analyzed from two perspectives. First, data reflecting the changes from before and after use was analyzed to identify immediate gains from using the system. This served to indicate individuals' increased ability to soothe and overcome feelings of anxiety. This data is rightfully impacted by all factors that contribute to anxiety reduction prior to a given dental procedure, and it is not a measure of increased autonomous effectiveness. Instead, any increase in effectiveness of the system. All eleven patients reported a significant reduction in anxiety and stress levels.

| Pre Dental Anxiety Data | | | |
|---|---|---|---|
| DESCRIPTION | MODERATE | HIGH | SEVERE |
| Patient #1 | — | — | 32 |
| Patient #2 | — | 17 | — |
| Patient #3 | — | 17 | — |
| Patient #4 | — | — | 33 |
| Patient #5 | — | 17 | — |
| Patient #6 | — | — | 29 |
| Patient #7 | — | — | 27 |
| Patient #8 | — | — | 30 |
| Patient #9 | — | — | 35 |
| Patient #10 | — | 16 | — |
| Patient #11 | — | — | 24 |

| Post Dental Anxiety Data | | | |
|---|---|---|---|
| DESCRIPTION | MODERATE | HIGH | SEVERE |
| Patient #1 | 7 | — | — |
| Patient #2 | 7 | — | — |
| Patient #3 | 11 | — | — |
| Patient #4 | 8 | — | — |
| Patient #5 | 8 | — | — |
| Patient #6 | 7 | — | — |
| Patient #7 | 9 | — | — |
| Patient #8 | 12 | — | — |
| Patient #9 | 14 | — | — |
| Patient #10 | 7 | — | — |
| Patient #11 | 13 | — | — |

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for producing a symmetrically mirrored video segment comprising:
   selecting a video segment;
   dividing said video segment into two equal segments;
   reducing said two equal segments with an aspect ratio equation that when converted creates a symmetrical mirrored video segment;
   adding an audio soundtrack to said symmetrical mirrored video segment;
   playing said symmetrical mirrored video segment on a viewing device.

2. The method for producing a symmetrically mirrored video segment according to claim 1 wherein said video segment is selected from the 720×1080, 1080×1920, 2K, 4K, or 8K or 12K video segments having an aspect ratio of: (1.43:1, 1.78:1, 1.85:1, 2.35:1 or 2.76:1).

3. The method for producing a symmetrically mirrored video segment according to claim 1 including the step of adding natural sounds in a computer based video editing software to create said video program.

4. The method for producing a symmetrically mirrored video segment according to claim 1 wherein mirrored video segment has an aspect ratio equation that when converted creates a symmetrical 720×1080, 1080×1920, 2K, 4K, 8K or 12K, (1.43:1, 1.78:1, 1.85:1, 2.35:1 or a 2.76:1), field of view.

5. The method for producing a symmetrically mirrored video segment according to claim 1 wherein said aspect ratio 1.43:1, 1.78:1, 1.85:1, 2.35:1 or 2.76:1), is maintained and a %50 reduction is applied to the horizontal field of view to the direct center of the 720×1080, 1080×1920, 2K, 4K, 8K or a 12K field of view.

6. The method for producing a symmetrically mirrored video segment according to claim 1 wherein said aspect ratio (1.43:1, 1.78:1, 1.85:1, 2.35:1 or 2.76:1), is maintained and the video segment is flipped horizontally and a %50 reduction is applied to the horizontal field of view to the direct center of the 720×1080, 1080×1920, 2K, 4K, 8K or a 12K field of view.

7. The method for producing a symmetrically mirrored video segment according to claim 1 wherein said flipped video segment is moved to the right corner of the 720×1080, 1080×1920, 2K, 4K, 8K or 12K, (1.43:1, 1.78:1, 1.85:1, 2.35:1 or a 2.76:1) aspect ratio field of view and the original segment is moved to the left corner of the 720×1080, 1080×1920, 2K, 4K, 8K or 12K, (1.43:1, 1.78:1, 1.85:1, 2.35:1 or a 2.76:1) aspect ratio field of view.

8. The method for producing a symmetrically mirrored video segment according to claim 1 wherein said flipped and original segments are place side by side at the center of a 720×1080, 1080×1920, 2K, 4K, 8K or a 12K field of view to create one symmetrically mirrored video segment.

9. The method for producing a symmetrically mirrored video segment according to claim 1 including the step of combining said mirrored video segment with other symmetrically mirrored video segments.

10. The method for producing a symmetrically mirrored video segment according to claim 1 wherein said symmetrically mirrored video segment is between three seconds and thirty minutes long.

11. The method for producing a symmetrically mirrored video segment according to claim 1 wherein said playing device is selected from the group of: video glasses, 3D software and 3D video glasses, 3D parallax software, micro SD memory cards, HD televsions, 3D televisions, virtual reality software and hardware, mobile media, computers and video streaming internet, widescreen cinema standard and IMAX theatrical projections.

* * * * *